United States Patent [19]

Mulder et al.

[11] 4,239,707
[45] Dec. 16, 1980

[54] NOVEL 8-SUBSTITUTED BICYCLO(3,2,)-OCTANES

[75] Inventors: Albertus J. Mulder, Amsterdam, Netherlands; Pieter A. Verbrugge, Houston, Tex.

[73] Assignee: Shell Oil Company, Houston, Tex.

[21] Appl. No.: 106,227

[22] Filed: Dec. 21, 1979

[30] Foreign Application Priority Data

Dec. 29, 1978 [GB] United Kingdom ............... 50280/78

[51] Int. Cl.³ .................... C07C 17/08; C07C 119/02
[52] U.S. Cl. .................................. 570/130; 260/464; 570/164; 570/187; 570/214
[58] Field of Search ............... 260/648 R (U.S. only), 260/ 648 F, 464

[56] References Cited
PUBLICATIONS

Whitesell et al., Tetrahedron Letters No. 19, pp. 1549–1550 (1976).

*Primary Examiner*—Delbert E. Gantz
*Assistant Examiner*—Joseph A. Boska

[57] ABSTRACT

Novel compounds of general formula (1)

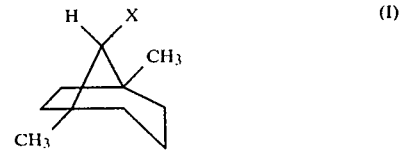

wherein X represents a F, Cl, Br, I or CN are of interest as heat stable ligands for catalytic systems. They can be prepared in good yields from 1,5-dimethyl-1,5-cyclooctadiene as well as from the corresponding bicyclic alcohol wherein X is OH.

8 Claims, No Drawings

NOVEL 8-SUBSTITUTED BICYCLO(3,2,)-OCTANES

BACKGROUND OF THE INVENTION

This invention relates to a novel class of 8-substituted bicyclo[3,2,1]octanes and to their preparation. More particularly, this invention is directed to novel 1,5-dimethyl-bicyclo[3,2,1]octane derivatives, substituted in the 8-position with halogen or cyanide substituents and to processes for their preparation starting with 1,5-dimethyl-1,5-cyclooctadiene or 1,5-dimethyl-bicyclo[3,2,1]octan-8-ol.

Certain 8-substituted 1,5-dimethyl-bicyclo[3,2,1]octane derivatives are known. For example, an article by J. K. Whitesell et al in Tetrahedron Letters No. 19 pp. 1549-1552 (1976) describes 8-hydroxy- and 8-tosyl-1,5-dimethylbicyclo[3,2,1]octane and their preparation from 1,5-dimethyl-1,5-cyclooctadiene. In this reference teaching, the 8-hydroxy-derivative is prepared by reacting the substituted cyclooctadiene with perchloric acid in a water-dioxane solution and the 8-hydroxy compound is subsequently converted to the tosylate by reaction with tosyl chloride in pyridine. Further, carboxylic acid esters of 1,5-dimethylbicyclo[3,2,1]octan-8-ol are described in copending U.S. Patent Application Ser. No. 37,196, filed May 8, 1979 (common assignee) as having distinctive aroma properties and utility as synthetic perfume materials. An attractive synthetic technique to preparation are these ester derivatives by hydrolysis or alcoholysis of 1,5-dimethyl-1,5-cyclooctadiene is disclosed in a second copending U.S. patent application (U.S. Ser. No. 37,195, filed May 8, 1979—common assignee).

SUMMARY OF THE INVENTION

A novel class of 8-substituted 1,5-dimethyl-bicyclo[3,2,1]octanes have now been found which are exceptionally heat stable and therefore of interest for use as ligand or ligand precursors in catalysts employed under severe process conditions. Further, certain of these novel bicyclooctane derivatives (the 8-bromo- and 8-iodo-compounds) are useful as starting materials or intermediates in the synthesis of aroma chemicals since they are readily converted in high yield to the corresponding 8-alkanoates disclosed in the aforementioned U.S. patent application Ser. No. 37,196 as having aroma chemical utility. This novel class of 1,5-dimethyl bicyclo-[3,2,1]octane derivatives is represented by the general formula

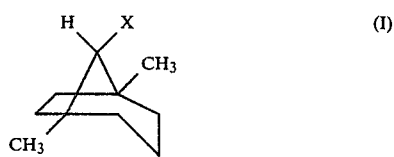

wherein X represents a halogen atom or a cyanide group. From a stereochemical standpoint, the invention encompasses compounds according to the general formula I in which the substituents H and X are in either the endo or exo position relative to the trimethylene grouping.

DESCRIPTION OF THE PREFERRED EMBODIMENTS

Compounds according to general formula I above wherein X is fluoro or chloro are especially preferred because they are not only heat stable but also virtually chemically inert which renders them particularly suitable for use as ligands in catalytic systems. Also preferred are the 8-bromo-, 8-iodo- and 8-cyano derivatives (compounds of the general formula I wherein X is bromo, iodo or cyano) since they can be converted by reaction with the appropriate alkanoic acid in the presence of a suitable catalyst to the corresponding 8-alkanoates which, in turn, are useful as aroma chemicals.

The compounds according to the present invention wherein X represents a chlorine, bromine or iodine moiety in general formula I above can be prepared by reacting 1,5-dimethyl-1,5-cyclooctadiene with a concentrated aqueous solution of the corresponding hydrogen halide. Normally, the reaction will be carried out at elevated temperatures in the presence of an acidic catalyst. In this regard good results have been obtained using an acidic ion-exchange resin such as AMBERLYST A15. Other well-known strong acidic ion-exchange resins can also be employed, e.g., ZEOCARB- or DOWEX-type resins. For highest conversions, the hydrogen halide is employed in at least equal molar ratios with the starting diene and preferably in a molar excess over the diene starting material.

The compound according to formula I wherein X represents a fluorine atom can be prepared in good yields starting from 1,5-dimethyl-1,5-cyclooctadiene using anhydrous hydrogen fluoride at reduced temperatures, e.g., $-10°$ to $5°$ C., in the presence of a polar solvent such as a lower alkanol or an ether. Examples of suitable lower alkanols comprise methanol and ethanol. Suitable ethers comprise diethylether and tetrahydrofuran. Good results can also be obtained using mixtures of lower alkanols and ethers as solvents, e.g., a mixture of methanol and tetrahydrofuran.

It is also advantageous to use a phase-transfer catalyst when the compounds of the invention are prepared using an aqueous hydrogen halide as is described above. Phase-transfer catalysts are reagents which are capable of accelerating interphase reactions in aqueous/organic two-phase systems. Phase-transfer catalysts which can be conveniently employed, e.g., in the preparation of 1,5-dimethyl-8- iodo-bicyclo[3,2,1]octane, include quaternary ammonium, phosphonium, arsonium and sulphonium compounds such as tetra-n-butylammonium chloride, tri-sec.octyl methylammonium chloride, tetramethylphosphonium iodide, methyl triphenylarsonium iodide, methyl dinonylsulfonium methylsulfate and n-hexa-decycldimethylsulfonium iodide.

The compounds prepared according to the above procedures are recovered using conventional working-up procedures, e.g., azeotropic distillation of the hydrogen halide employed followed by one or more extractions of the residue, e.g., with an alkane such as pentene or hexane. After drying and removal of the extractant, the bicyclic halide can be readily isolated by fractional distillation, e.g., fractional distillation under reduced pressure.

A further method of preparing compounds according to formula I wherein X represents a chlorine, bormine or iodine moiety comprises reacting the corresponding 8-hydroxy compound:

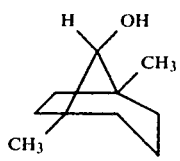 (II)

with an appropriate halogenating agent. It will be appreciated that the groups H and OH also will be in the endo or exo position vis a vis the trimethylene group. As mentioned above, the 8-hydroxy compound and its preparation is known from Tetr. Lett., No. 19 (1976) pp. 1549–52.

In specific instances, 1,5-dimethyl-8-chlorobicyclo[3,2,1]-octane can be suitable prepared by reacting the 8-hydroxy compound (formula II, above) with phosphorus pentachloride or thionylchloride in the presence of pyridine or with concentrated hydrogen chloride in the presence of a heavy metal chloride such as zinc chloride. The corresponding 8-bromo derivative can be suitable prepared by reacting the 8-hydroxy compound with phosphorus pentabromide, or thionylbromide in the presence of pyridine or with concentrated hydrogen bromide in the presence of an acidic catalyst such as sulfuric acid or an acidic ion-exchange resin. The corresponding 8-iodo derivative can be suitably prepared by reacting the 8-hydroxy compound with potassium iodide in the presence of polyphosphoric acid or phosphorus and iodine or with hydrogen iodide in the presence of an acidic catalyst.

It has been found that the 8-fluoro derivative (compound according to formula I wherein X is fluoro) cannot be prepared directly from the 8-hydroxy compound (formula II, above). A method of preparing 1,5-dimethyl-8-fluorobicyclo[3,2,1]octane comprises reacting the corresponding 8-iodo compound with potassium fluoride in a high boiling aprotic solvent such as hexamethylene phosphoramide, N-methylpyrolidone or dimethylformamide.

The compound according to formula I wherein X represents a cyanide group can be prepared from the corresponding 8-bromo or 8-iodo compound using copper(I) cyanide optionally in the presence of high boiling aprotic solvent such as dimethylformamide.

The 8-bromo and the 8-iodo-compounds can be used as starting materials for the preparation of the corresponding 8-alkanoates. Thus, 1,5-dimethyl-8-acetoxy bicyclo[3,2,1]octane can be prepared by refluxing the 8-bromo- or 8-iodo-compound in acetic acid in the presence of sodium acetate. Cu(I) salts such as copper(I) chloride can be used conveniently as catalysts in this reaction. As mentioned above, 8-alkanoates are of interest as aroma chemicals.

The starting material 1,5-dimethyl-1,5-cyclooctadiene can be prepared by dimerizing isoprene as mentioned in French patent specification No. 1,283,217 and Netherlands patent specification No. 7800529. The presence of the isomeric compound 1,6-dimethyl-1,5-cyclooctadiene can be tolerated in the starting material without adversely effecting the yield of the desired 8-substituted bicyclo[3,2,1]octane derivative. It has been found that mixtures containing ca 25% by weight of 1,6-dimethyl-1,5-cycloctadiene can be suitably employed.

The present invention is illustrated by means of the following Examples.

EXAMPLE 1

Preparation of 1,5-dimethyl-8-chlorobicyclo[3,2,1]octane. (a) A mixture of 1,5-dimethyl-1,5-cyclooctadiene and 1,6-dimethyl-1,5-cyclooctadiene, 13.6 g (0.1 mol), ratio 80/20, was boiled under reflux while stirring with 100 ml 38% hydrochloric acid and 1 g of AMBERLYST A15 ion-exchange resin. Thereafter the reaction product was subjected to azeotropic distillation with 38% hydrochloric acid. The distillate was then extracted with pentane. The pentane layer obtained was washed with water and an aqueous sodium bicarbonate solution. After drying over anhydrous sodium sulphate and boiling down the solvent, the residue was subjected to a fractional distillation under reduced pressure. 11.5 g of product was obtained (b.p. 75° C./7mm Hg). The yield, calculated on the amount of 1,5-dimethyl-1,5-cyclooctadiene added to the reaction was 83%. The purity according to gas-liquid chromatography was more than 95%.

The structure of the compound was confirmed by infra-red and nuclear magnetic resonance spectroscopy.

I.R.: 2980, 2930, 1460, 1380, 830 and 780 cm$^{-1}$.

N.M.R. (ppm): 1.00 (2×CH$_3$, s); 1.30–1.70(5×CH$_2$, m) and 3.53(1×H, s).

(b) 1,5-dimethyl-8-chloro bicyclo[3,2,1]octane was also obtained by reacting 1,5-dimethyl-8-hydroxybicyclo[3,2,1]octane with thionyl-chloride in the presence of pyridine. The structure was again determined and confirmed by I.R. and N.M.R.-analysis. The compound appeared to be very stable and remained inert when heated with concentrated potassium hydroxide or when boiling with 60% sulfuric acid.

EXAMPLE 2

Preparation of 1,5-dimethyl-8-bromo bicyclo[3,2,1]octane.

(a) A mixture of 68 g (0.5 mol) 1,5-dimethyl-1,5-cyclooctadiene and 1,6-dimethyl-1,5-cyclooctadiene (ratio 80/20) was boiled under stirring for 1 hour with 500 ml 48% hydrogen bromide and 10 g of AMBERLYST A15 ion-exchange resin. Thereafter, the reaction product was subjected to azeotrope distillation with the aqueous hydrogen bromide solution. The distillate was then extracted with pentane. The pentane layer was treated as described in Example 1a. By fractional distillation under reduced pressure 81 g 1,5-dimethyl-8-bromobicyclo[3,2,1]octane (b.p. 93° C./10 mm Hg) was obtained in 93.3% yield. The purity of the product according to gas-liquid chromatography was more than 98%.

The structure of the compound was confirmed by I.R. and N.M.R.-analysis:

I.R. 2980, 2930, 1460, 1385, 830, 760 and 705 cm$^{-1}$.

N.M.R.: (ppm): 1.00 (2×CH$_3$, s), 1.25–1.75 (5×CH$_2$, m) and 3.75 (1×H, s).

(b) 1,5-dimethyl-8-hydroxy bicyclo[3,2,1]octane (13.6 g (0.1 mol)) was boiled with 50 ml 48% hydrogen bromide for 4 hours under stirring in the presence of 1 g AMBERLYST A15 ion-exchange resin. The reaction product was extracted after cooling with pentane. The pentane layer was washed with water and a diluted sodium bicarbonate solution. After drying over anhydrous sodium sulfate and boiling down pentane the residue was subjected to fractional distillation under reduced pressure. 18.5 g 1,5-dimethyl-8-bromobicyclo[3,2,1]octane was obtained in 85.1% yield (b.p. 93° C./10 mm Hg). The product obtained was identical with the compound according to the process described in Example 2a.

EXAMPLE 3

Preparation of 1,5-dimethyl-8-iodobicyclo[3,2,1]octane.

(a) A mixture of 13.6 g (0.1 mol) of 1,5-dimethyl-1,5-cyclooctadiene and 1,6-dimethyl-1,5-cyclooctadiene, ratio 80/20, was boiled under reflux while stirring for two hours with 100 ml 55% hydrogen iodide in the presence of 2 g AMBERLYST A15 ion-exchange resin. The reaction product was extracted with pentane after cooling. The pentane layer was washed with water and an aqueous sodium bicarbonate solution. Residual free iodine present in the solution was washed away with a diluted sodium thiosulfate solution. The resulting pentane solution was dried over anhydrous sodium sulfate and pentane was flashed off. Fractional distillation under reduced pressure gave 17 g of 1,5-dimethyl-8-iodobicyclo[3,2,1]octane (b.p. 106° C./7 mm Hg). Yield 80.6% calculated on the amount of 1,5-dimethyl-1,5-cyclooctadiene added to the reaction. The purity of the product according to gas-liquid chromatography was more than 95%. The product appeared to be sensitive to day-light.

The structure of the compound was confirmed by I.R. and N.M.R. analysis:

I.R.: 2960, 2940, 1450, 1380, 730 and 680 cm$^{-1}$.

N.M.R. (ppm): 1.00 (2×CH$_3$, s), 1.25–1.75 (5×CH$_2$, m) and 3.87 (1×H, s).

(b) 1,5-dimethyl-8-iodobicyclo[3,2,1]octane was also obtained by reacting 1,5-dimethyl-8-hydroxybicyclo-[3,2,1]octane with potassium iodide in the presence of polyphosphoric acid. The structure was again determined and confirmed by I.R. and N.M.R. analysis.

EXAMPLE 4

Preparation of 1,5-dimethyl-8-fluorobicyclo-[3,2,1]octane.

A mixture of 13.6 g (0.1 mol) 1,5-dimethyl-1,5-cyclooctadiene and 1,6-dimethyl-1,5-cyclooctadiene (ratio 80/20 was dissolved in a mixture of tetrahydrofuran (15 ml) and methanol (5 ml). The resulting mixture was added dropwise under stirring and cooling to 50 ml anhydrous hydrogen fluoride. The temperature was kept at about −10° C. during the addition (45 min). After the addition, the reaction mixture was stirred for a further period of 15 minutes at 0° C. and then poured into a cooled saturated solution of potassium acetate in water. The upper layer was then decanted and the aqueous layer was extracted several times with pentane. The upper layer and the pentane solutions were combined and washed with water and an aqueous diluted solution of sodium bicarbonate (5%). The pentane layer was then treated as described in Example 1a which resulted in 10.8 g of 1,5-dimethyl-8-fluorobicyclo-[3,2,1]octane (b.p. 68°–69° C./22 mm Hg) or a yield of 86.5% based on the starting 1,5-dimethyl-1,5-cyclooctadiene. The purity of the product according to gas-liquid chromatography was more than 98%.

The structure of the compound was confirmed by I.R. and N.M.R. analysis.

I.R.: 2980, 2930, 1480, 1380, 1170, 1110, 1050 and 970 cm$^{-1}$.

N.M.R.: (ppm): 1.00 (2×CH$_3$, s) 1.20–1.60 (5×CH$_2$, m) and 3.65 and 4.27 (1×H, s) split up due to H-F coupling).

The compound appeared to be very stable and remained inert when treated in the manner as described in Example 1b.

EXAMPLE 5

Preparation of 1,5-dimethyl-8-bromobicyclo[3,2,1]octane.

In a 100 ml three-necked flask equipped with a magnetic stirrer, a thermometer and a dropping funnel was placed 50 g of a 45–48% aqueous hydrogen bromide solution together with a few crystals of tetra-n-butyl ammonium chloride. Under vigorous stirring 13.6 g (0.1 mol) 1,5-dimethyl-1,5-cyclooctadiene and 1,6-dimethyl-1,5-cyclooctadiene (ratio 80/20) was added over a period of 15 minutes during which an exothermic reaction occurred. After the reaction had subsided, the reaction mixture was extracted with pentane. The pentane extract obtained was washed neutral with water and diluted sodium aqueous bicarbonate. After drying over anhydrous sodium sulfate and removal of the solvent by distillation, 20.4 g of a slightly brown-colored oil was obtained which consisted predominantly of 1,5-dimethyl-8-bromobicyclo[3,2,1]octane.

EXAMPLE 6

Preparation of 1,5-dimethyl-8-iodobicyclo[3,2,1]octane.

In a 250 ml three-necked flask equipped with a magnetic stirrer, a thermometer and a dropping funnel was charged with 72 g of a 55% aqueous hydrogen iodide solution. After the addition of 10 mg of tetra-n-butyl ammonium chloride, 28 g (about 0.2 mol) 1,5-dimethyl-1,5-cyclooctadiene and 1,6-dimethyl-1,5-cyclooctadiene (ratio 80/20) was added dropwise under vigorous stirring while the temperature was maintained below 55° C. After the reaction had subsided, the reaction mixture was worked up in the manner as described in Example 5. A slightly red-colored residue (47 g) was obtained which consisted of more than 90% of 1,5-dimethyl-8-iodobicyclo[3,2,1]octane. The structure was confirmed by I.R. and N.M.R. analysis.

EXAMPLE 7

Preparation of 1,5-dimethyl-8-acetoxybicyclo[3,2,1]octane.

5 g of 1,5-dimethyl-8-bromobicyclo[3,2,1]octane was boiled under reflux for 18 hours in acetic acid in the presence of sodium acetate and copper(I) chloride. The reaction mixture was cooled and filtered, diluted with water and extracted with pentane. The pentane solution was washed with water and an aqueous sodium bicarbonate solution, dired, evaporated and fractionally distilled. 1,5-dimethyl-8-acetoxy-bicyclo[3,2,1]octane was obtained in good yield. 1,5-dimethyl-8-acetoxybicyclo[3,2,1]octane was also obtained in a similar manner starting from the 8-iodo compound described in Example 3.

What is claimed is:

1. 1,5-Dimethylbicyclo[3,2,1]octanes of the formula I:

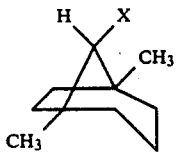 (I)

wherein X represents a halogen atom selected from the class consisting of fluorine, chlorine, bromine and iodine or a cyanide group.

2. The 1,5-dimethylbicyclo[3,2,1]octane according to claim 1 wherein X is chlorine or fluorine.

3. The 1,5-dimethylbicyclo[3,2,1]octane according to claim 1 wherein X is bromine or iodine.

4. 1,5-Dimethyl-8-chlorobicyclo[3,2,1]octane.

5. 1,5-Dimethyl-8-fluorobicyclo[3,2,1]octane.

6. A process for the preparation of 1,5-dimethylbicyclo[3,2,1]- octanes according to claim 1 wherein X represents a chlorine, bromine or iodine moiety which comprises reacting 1,5-dimethyl-1,5-cyclooctadiene with a concentrated aqueous solution of the corresponding hydrogen halide.

7. The process according to claim 6 wherein the reaction of 1,5-dimethyl-1,5-cyclooctadiene with the corresponding hydrogen halide is carried out in the presence of an acidic ion-exchange resin or a phase-transfer catalyst.

8. A process for the preparation of 1,5-dimethyl-8-fluorobicyclo[3,2,1]octane which comprises reacting 1,5-dimethyl-1,5-cyclooctadiene with anhydrous hydrogen fluoride in the presence of a polar solvent.

* * * * *